(12) United States Patent
Tavolacci et al.

(10) Patent No.: US 8,870,841 B2
(45) Date of Patent: Oct. 28, 2014

(54) DISPOSABLE DIAPER WITH ATTACHED WRAPPER FOR ENCLOSING AND SEALING THE DIAPER WHEN SOILED

(76) Inventors: Danielle Tavolacci, Mount Kisco, NY (US); Steve J. Tavolacci, Mount Kisco, NY (US)

( * ) Notice: Subject to any disclaimer, the term of this patent is extended or adjusted under 35 U.S.C. 154(b) by 421 days.

(21) Appl. No.: 13/332,581

(22) Filed: Dec. 21, 2011

(65) Prior Publication Data
US 2013/0035657 A1 Feb. 7, 2013

Related U.S. Application Data

(60) Provisional application No. 61/515,378, filed on Aug. 5, 2011.

(51) Int. Cl.
| A61F 13/15 | (2006.01) |
| A61F 13/20 | (2006.01) |
| B31D 1/06 | (2006.01) |
| B31D 1/00 | (2006.01) |
| A61F 13/551 | (2006.01) |

(52) U.S. Cl.
CPC ............... B31D 1/0081 (2013.01); B31D 1/06 (2013.01); *A61F 2013/55125* (2013.01); *A61F 13/5511* (2013.01)
USPC ............. 604/385.13; 604/385.06; 604/385.19

(58) Field of Classification Search
CPC ... A61F 13/551; A61F 13/5512; A61F 13/84; A61F 13/5515; A61F 13/505; A61F 13/5518; A61F 2013/8402; A61F 13/5513; A61F 2013/55195; A61F 13/5517

USPC ............................ 604/385.06, 385.13, 385.19
See application file for complete search history.

(56) References Cited

U.S. PATENT DOCUMENTS

| 584,204 | A | * | 6/1897 | Bowles ........................ 604/397 |
| 3,369,545 | A | | 2/1968 | Wanberg |
| 3,604,423 | A | * | 9/1971 | Fraser ....................... 604/385.13 |
| 3,890,973 | A | * | 6/1975 | Davis et al. .................. 604/355 |
| 3,920,019 | A | | 11/1975 | Schaar |
| 4,559,051 | A | * | 12/1985 | Hanson .................... 604/385.03 |
| 4,581,027 | A | | 4/1986 | Alvarado |
| 4,604,096 | A | | 8/1986 | Dean et al. |
| 4,808,175 | A | | 2/1989 | Hansen |
| 4,923,455 | A | | 5/1990 | Dean et al. |
| 4,931,052 | A | * | 6/1990 | Feldman ................. 604/385.06 |
| 4,968,312 | A | * | 11/1990 | Khan ....................... 604/385.13 |
| 5,037,414 | A | * | 8/1991 | Booth ..................... 604/385.13 |
| 5,141,505 | A | * | 8/1992 | Barrett .................... 604/385.13 |
| 5,950,636 | A | * | 9/1999 | Hickey ........................ 132/200 |
| 6,596,107 | B2 | | 7/2003 | Stopher |
| 6,820,283 | B2 | | 11/2004 | Graneto, III |

* cited by examiner

*Primary Examiner* — Michele M Kidwell
(74) *Attorney, Agent, or Firm* — Karl F. Milde, Jr.; Eckert Seamans Cherin & Mellott, LLC

(57) ABSTRACT

A disposable diaper is provided with a wrapper in the shape of a shower cap, enabling a user to wrap and seal the diaper when soiled. The wrapper is attached to either the front or back waistband region of the diaper. Flexible strands, secured to the wrapper and extending outward on opposite sides of its central opening, may be tied together to close the opening and fully seal the package or pouch when the soiled diaper is inserted.

20 Claims, 5 Drawing Sheets

DISPOSABLE DIAPER WITH ATTACHED WRAPPER FOR ENCLOSING AND SEALING THE DIAPER WHEN SOILED

CROSS-REFERENCE TO RELATED APPLICATION

This application claims priority from Provisional Application No. 61/515,378 filed Aug. 5, 2011.

BACKGROUND OF THE INVENTION

The present invention relates to an improvement in a disposable diaper which allows a user to wrap and seal the diaper when soiled.

More particularly, the present invention relates to a diaper with an attached diaper wrapper, permitting the user to enclose and seal the diaper prior to disposal to avoid mess and odor.

Disposable diapers are well known in the art. Such diapers include a front waistband region, a back waistband region, and an intermediate region with two laterally opposed side margins interconnecting the front and back waistband regions. The intermediate region of the diaper has a liquid pervious liner, a liquid impervious backsheet and an absorbent core disposed between the liner and the backsheet.

When soiled by a wearer, the disposable diaper is normally disposed of by folding or rolling it into a packet which contains the liquid and/or solid waste and then dropping it into a liquid-impervious plastic trash bag. This disposal method is quite satisfactory if a trash container with a trash bag liner is close at hand. However, a diaper must often be changed, and the soiled diaper disposed of, while the wearer is in transit and such a trash bag is not readily available.

Various attempts have been made to design disposable diapers with an integrated means for wrapping and sealing the diaper when it is soiled. One such means is disclosed in the U.S. Pat. No. 4,923,455 entitled "Disposable Diaper with Integral Disposal Envelope". This patent teaches attaching an "envelope" or bag-shaped container to one side of the diaper. When the diaper is soiled, it is folded and inserted inside the envelope. The edge of the envelope is provided with a seam that serves to close and seal the bag when the used diaper is inserted.

Disposable diapers with this type of wrapping device have not seen common commercial use because they add substantially to the cost of producing the diaper and are somewhat cumbersome to use.

SUMMARY OF THE INVENTION

It is an object of the present invention to provide an inexpensive article, adapted to be used with a disposable diaper, which permits the diaper, when soiled, to be wrapped and sealed in a convenient way.

It is a further object of the present invention to provide a wrapper for a disposable diaper which enables the user to completely enclose and seal the diaper prior to disposal.

It is a further object of the present invention to provide a disposable diaper with an attached diaper wrapper that is inexpensive to produce, extremely easy to use and provides a sanitary way to dispose of the soiled diaper.

This object, as well as other objects which will become apparent from the discussion that follows, are achieved, in accordance with the present invention, by providing a wrapper in the shape of a "shower cap", adapted to be attached to either the front or back waistband region of a disposable diaper and having flexible strands on opposite sides of the opening in the wrapper to allow the user to fully seal the package or pouch when the soiled diaper is inserted.

More particularly, the present invention provides a wrapper for a disposable diaper which comprises the following elements:

(a) a liquid impervious, disc-shaped, flexible sheet with a rounded outer periphery having a first width when laid flat;

(b) an elastic strand secured to said outer periphery of the flexible sheet, said elastic strand forming a endless loop which, in its relaxed state, shapes the flexible sheet into a pouch with an opening inside of said loop having a second width less than or substantially equal to a distance between said two side margins of said diaper; and (c) a pair of flexible strands secured to the flexible disc on opposite sides of said opening and extending away from each other in opposite directions.

The first width of the flexible sheet is at least twice the second width of the opening such that, when shaped into a pouch, the flexible sheet is caused to assume a round pocket shape having an outer, annular portion folded over with said opening at its center. The annular portion of the flexible sheet is attached to one of the front and back waistband portions of the diaper. When the annular portion is so attached, the flexible strands, which are disposed on opposite sides of the opening, extend outward substantially perpendicularly to the side margins of the diaper.

With this arrangement, the diaper, when soiled, may be inserted in the pouch and the opening in the pouch may be closed by tying the flexible strands, thereby wrapping and sealing the soiled diaper.

According to one preferred embodiment of the present invention, the annular portion of the flexible sheet is attached to either the front or back waistband region of the diaper by means of an adhesive, by the application of heat and pressure, by sewing stitches or by any other means.

In another preferred embodiment of the present invention, the wrapper is enclosed in a wrapper cover that surrounds, protects and seals the wrapper. The enclosed wrapper may be sold as a separate commercial item or, alternatively, the cover may be attached to one of the front and back waistband regions of the diaper.

The flexible strands used for closing the opening in the wrapper are preferably made of a liquid impervious material, such as plastic, and are folded around the elastic band and attached to both sides of the flexible sheet, for example, by means of an adhesive, by the application of heat and pressure or by sewing stitches.

Finally, according to still another preferred embodiment of the present invention, the flexible sheet is made of an impervious material such as plastic.

It will be seen that the flexible sheet with the elastic band assumes a structure similar to that of a shower cap. In fact, a shower cap, when made in quantity by mechanical production equipment, is extremely inexpensive. Upon attaching suitable flexible strands to the opening of the shower cap, the cap may be simply attached to a disposable diaper in a final manufacturing step in producing the diaper.

For a full understanding of the present invention, reference should now be made to the following detailed description of the preferred embodiments of the invention as illustrated in the accompanying drawings.

DESCRIPTION OF THE PREFERRED EMBODIMENTS

Figure 1:
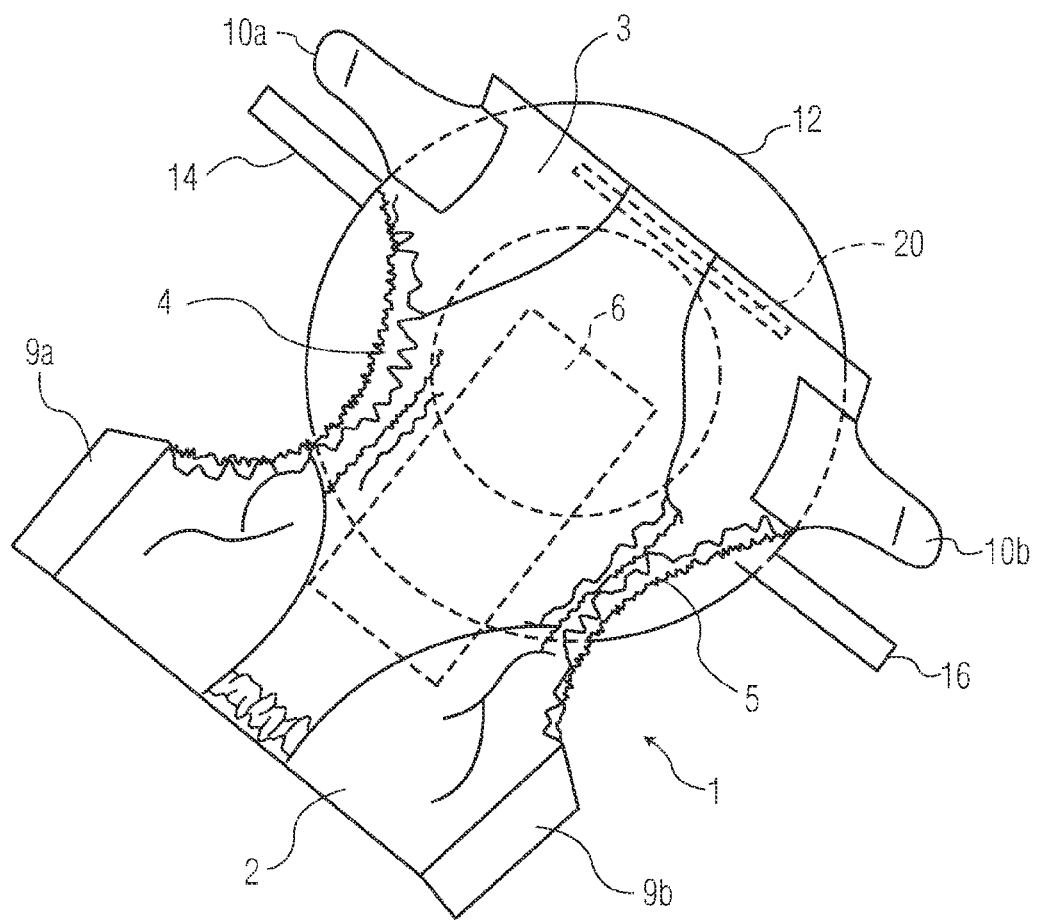
FIG. 1 is a perspective view of the disposable diaper with an attached wrapper according to a preferred embodiment of the present invention.

The preferred embodiments of the present invention will now be described with reference to FIGS. 1-8 of the drawings. Identical elements in the various figures are designated with the same reference numerals.

Figure 1A:
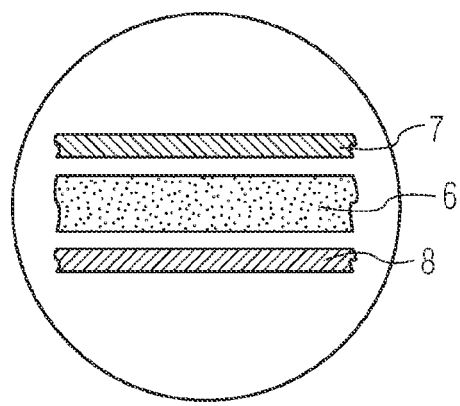

FIG. 1 shows a disposable diaper with an attached wrapper for enclosing and sealing the diaper when soiled. The disposable absorbent diaper 1 has a front waistband region 2, a back waistband region 3 and an intermediate region with two laterally opposed side margins 4 and 5, respectively, interconnecting the front and back waistband regions. As shown in FIG. 1a, the intermediate region of the diaper has a liquid pervious liner 7, a liquid impervious backsheet 8 and an absorbent core 6 interposed between the liner and the backsheet.

The front waistband region 2 has tabs 9a and 9b on opposite sides. The back waistband region 3 has matching tabs 10a and 10b on opposite sides. The tabs 9a and 10a are attachable together and the tabs 9b and 10b are attachable together to retain the diaper on an infant.

According to one embodiment of the present invention, the diaper further includes a wrapper 12 with attached, oppositely directed flexible strands 14 and 16 for enclosing and sealing the diaper when soiled.

Figure 2:
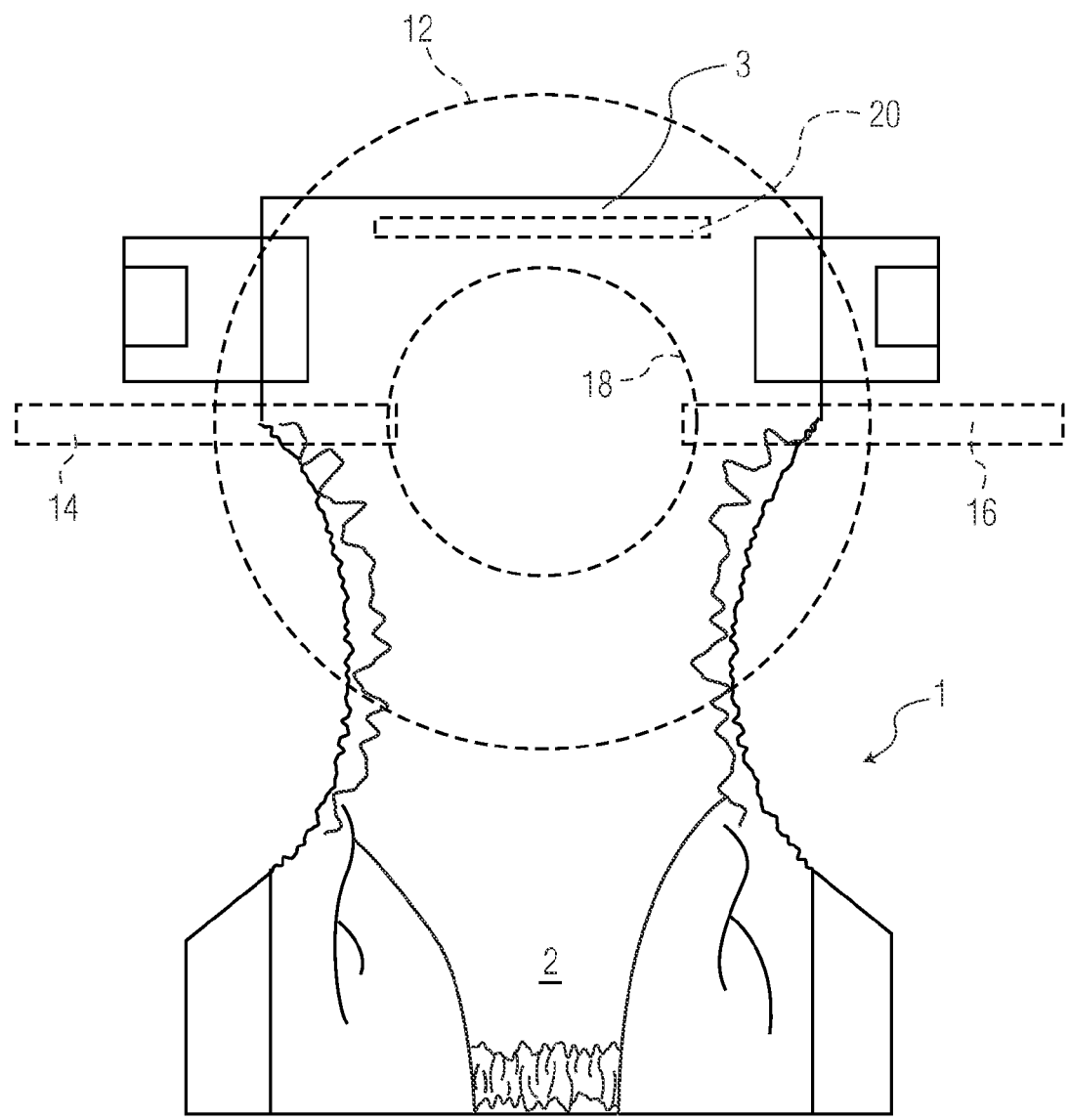
FIG. 2 is a top view of the disposable diaper of FIG. 1 with the attached wrapper shown in dashed lines.
Figure 4:
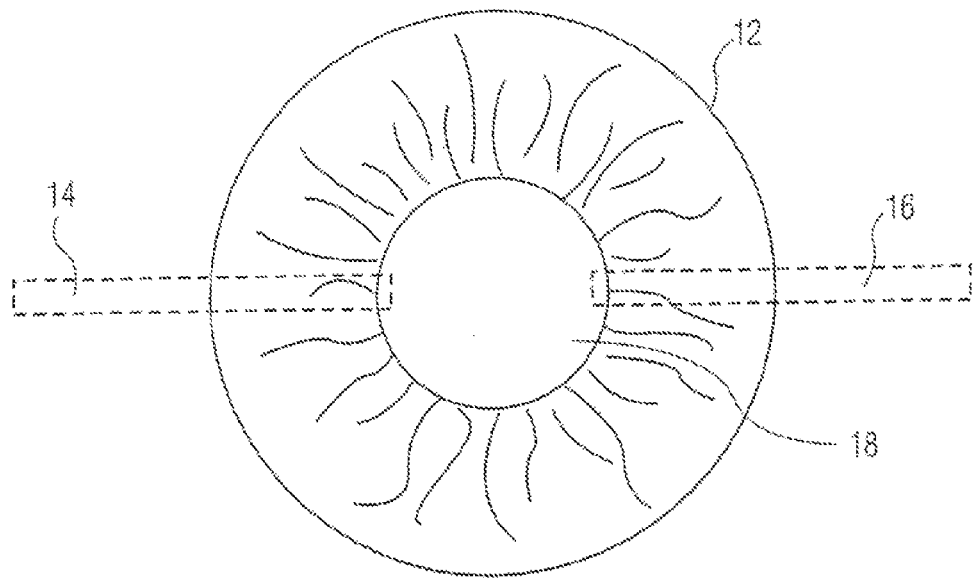
FIG. 4 is a top view of a shower cap with attached strands extending outward in opposite directions, for wrapping and sealing a soiled diaper in accordance with the present invention.

As is best seen in FIG. 2, which is a plan view of the diaper 1 with the wrapper 12 indicated in dashed lines, and Fig 4 which shows the wrapper 12 alone, the wrapper has an opening 18 at the center for receiving the soiled diaper. The wrapper 12 may be attached to either the front or back waistband of the diaper, as indicated by the dashed lines 20 in FIG. 2, by means of an adhesive, by the application of heat and pressure and/or by sewing stitches.

Figure 5:
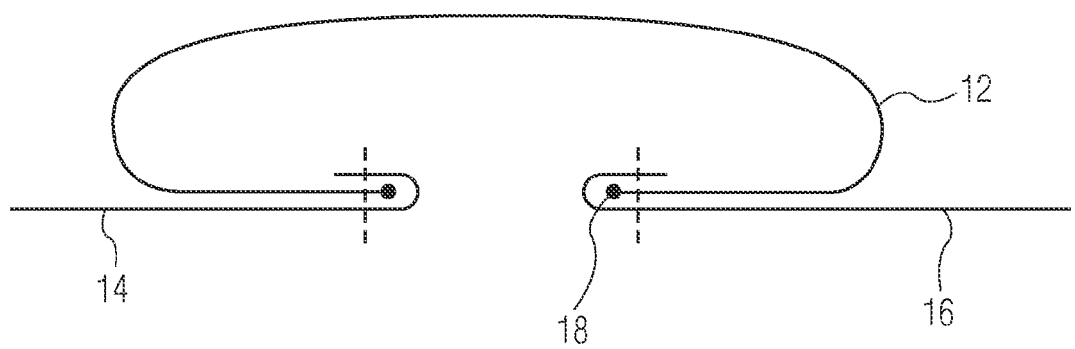
FIG. 5 is a representational, cross-sectional diagram showing a shower cap and attached strands in cross section, with the strands wrapped around the edge of the shower cap at the opening.

The flexible strands 14 and 16 are preferably ribbon shaped and liquid impervious. They are preferably made of durable plastic sheet, for example. As shown in FIG. 5, the strands are preferably folded around the inner edge of the opening 18 of the wrapper 12. They can be secured to the wrapper 12 by an adhesive, by heat and pressure and/or by sewing stitches.

Figure 3:
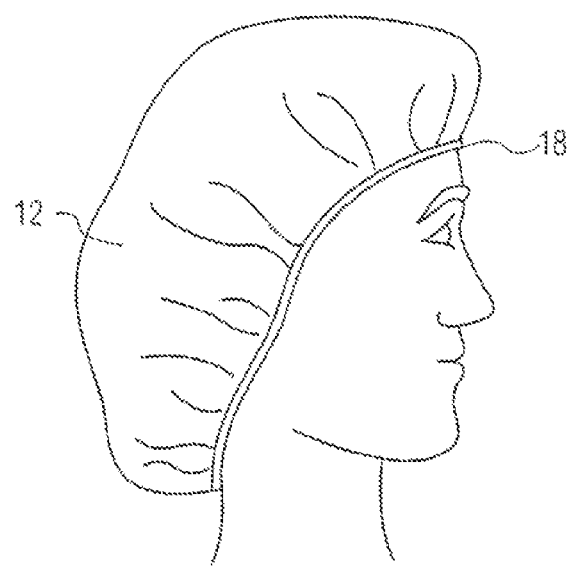
FIG. 3 is a side view of a typical shower cap which may be used with the present invention.

In this preferred embodiment of the present invention, the wrapper 12 takes the form of a conventional shower cap as shown in FIG. 3. This cap is formed by a liquid impervious, circular or oval shaped flexible sheet. An elastic strand is secured to the periphery of the opening 18 for the head, forming an endless loop which, in its relaxed state, shapes the flexible sheet into a pouch with the opening inside of the loop. The width of this opening 18 is preferably less than, or substantially equal to, the distance between the two side margins 4 and 5 of the diaper to be wrapped.

Preferably, the width of the flexible sheet when laid flat, without the elastic strand, is at least twice the width of the opening, such that, when shaped into a pouch, as shown in FIG. 4, the flexible sheet is thereby caused to assume a rounded pocket or pouch shape having an outer, annular portion folded over with the opening 18 at the middle.

Since shower caps, which are either substantially circular or oval shaped when laid flat, are produced in great quantities, they provide an inexpensive starting point for producing a wrapper for a disposable diaper. It is necessary only to attach the strands 14 and 16 and, thereafter, to attach the wrapper to a disposable diaper at the end of the diaper manufacturing process.

The wrapper can also be an individual article of commerce, sold separately from a disposable diaper and used for the same purpose of enclosing and sealing a diaper.

Figure 6:
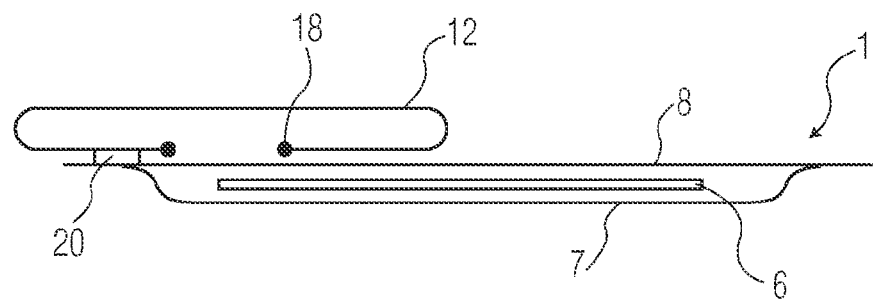
FIG. 6 is a representational, cross-sectional diagram showing a disposable diaper with an attached wrapper according to the preferred embodiment of the present invention.

FIG. 6 illustrates, in cross-section, how the wrapper 12 is attached to the impervious backsheet 8 of a diaper 1 which, as shown, includes a pervious layer 7 and an absorbent layer 6. The attachment 20 is by any conventional means, such as by an adhesive, by the application of heat and pressure, and/or by sewing stitches.

Figure 6A:
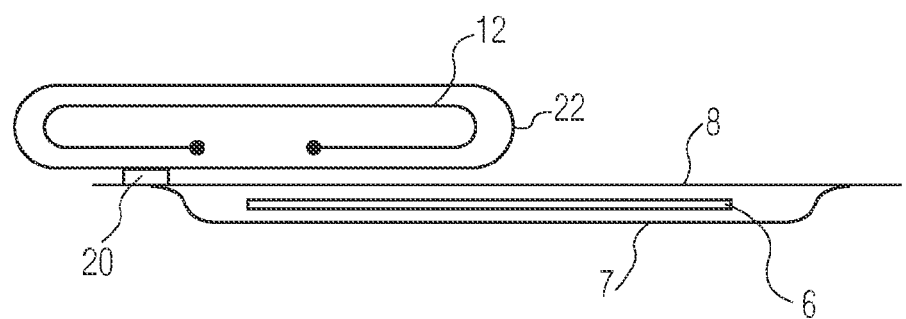
FIG. 6A is a representational, cross-sectional diagram showing an alternative embodiment of the disposable diaper with the wrapper enclosed in a protective cover which, in turn, is attached to the diaper.

FIG. 6A illustrates an alternative embodiment wherein the wrapper 12 is enclosed in a protective cover 22 which, in turn, is attached to the diaper 1 by a attachment means 20. The protective cover is preferably made of a liquid-impervious material.

Figure 7:
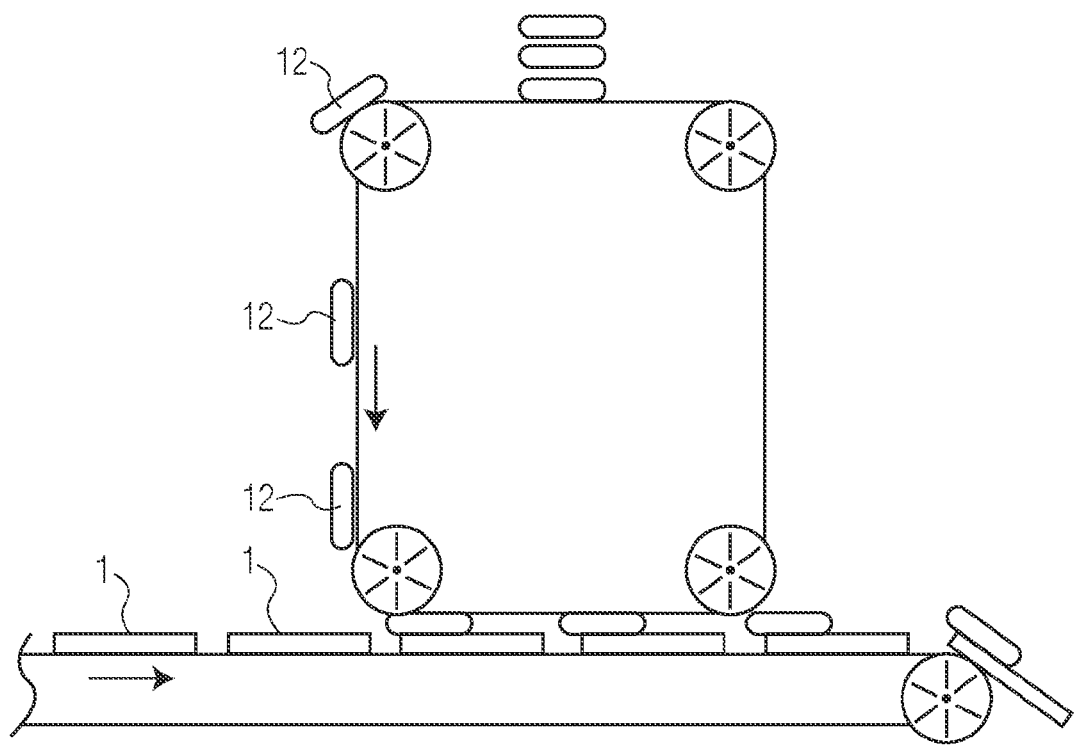
FIG. 7 is a representational diagram showing the final step in the manufacture of a disposable diaper and attached wrapper according to the present invention.

The wrapper 12 can be attached to the diaper 1 in a final manufacturing step, as indicated by the dual conveyor system shown in FIG. 7.

Figure 8:
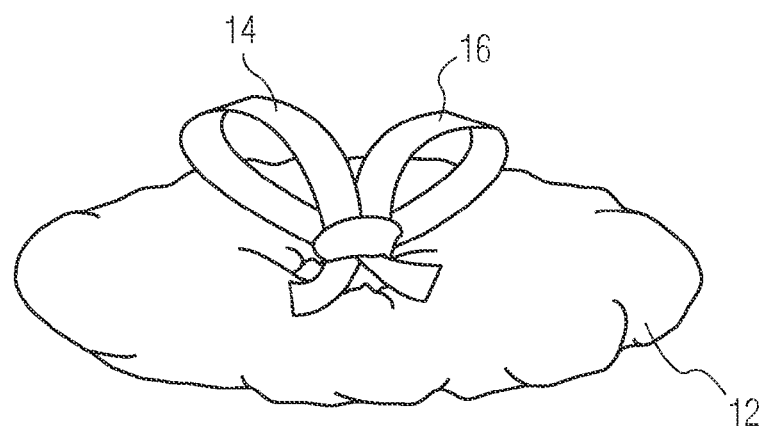
FIG. 8 is a perspective view of closed and sealed wrapper according to the invention, forming a pouch containing a soiled disposable diaper.

FIG. 8 shows a wrapper 12 with its opening 18 closed by the strands 14 and 16, thereby sealing its contents: the soiled diaper. When closed and sealed in this way, there is neither mess nor odor and the package can be retained for later disposal.

There has thus been shown and described a novel disposable diaper with attached wrapper for enclosing and sealing the diaper when soiled which fulfills all the objects and advantages sought therefore. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow.

What is claimed is:

1. A disposable absorbent diaper including a front waistband region, a back waistband region, and an intermediate region with two laterally opposed side margins interconnecting the front and back waistband regions, the intermediate region of the diaper having a liquid pervious liner, a liquid impervious backsheet and an absorbent core disposed between the liner and the backsheet, said diaper further including a wrapper for enclosing and sealing the diaper when soiled, with said wrapper comprising:

(a) a liquid impervious, disc-shape flexible sheet with a rounded, outer periphery having a first width when laid flat;
(b) an elastic strand secured said outer periphery of the flexible sheet, said elastic strand forming an endless loop which, in a relaxed state thereof, shapes the flexible sheet into a pouch with an opening inside of side loop having a second width less than or substantially equal to a distance between said two side margins of said diaper; and
(c) a pair of flexible strands secured to the flexible sheet on opposite sides of said opening and extending away from each other in opposite directions;
wherein said first width of the flexible sheet is at least twice said second width of said opening such that, when shaped into a pouch, said flexible sheet is thereby caused to assume a rounded pocket shape having an outer, annular portion folded over with said opening at a center portion thereof;
whereby said diaper, when soiled, may be inserted in said pouch and the opening in said pouch may be closed by tying said flexible strands, thereby wrapping and sealing the soiled diaper.

2. The diaper defined in claim 1, wherein said annular portion of the flexible sheet is attached to one of the front and back waistband and regions of the diaper.

3. The diaper defined in claim 2, wherein, when said annular portion is so attached, said flexible strands which are disposed on opposite sides of the opening, extend outward and substantially perpendicularly to the side margins of the diaper.

4. The diaper defined in claim 2, wherein said annular portion of the flexible sheet is attached to the diaper by at least one of an adhesive, the application of heat and pressure, and by sewing stitches.

5. The diaper defined in claim 1, further comprising a wrapper cover attached to one of the front and back waistband regions of the diaper which covers and surrounds said wrapper, said wrapper cover forming a container for said wrapper until said wrapper is removed for use.

6. The diaper defined in claim 1, wherein said flexible strands are liquid impervious.

7. The diaper defined in claim 6, wherein said flexible strands are made of plastic.

8. The diaper defined in claim 1, wherein said flexible strands are ribbon-shaped and are folded around the elastic strand and attached to both sides of the flexible sheet.

9. The diaper defined in claim 1, wherein said flexible strands are secured by an adhesive.

10. The diaper defined in claim 1, wherein said flexible strands are secured by application of heat and pressure.

11. The diaper defined in claim 1, wherein said flexible strands are secured by sewing stitches.

12. The diaper defined in claim 1, wherein said flexible sheet is made of plastic.

13. The diaper defined in claim 1, wherein said flexible sheet is substantially circular when laid flat.

14. The diaper defined in claim 1, wherein said flexible sheet is oval-shaped when laid flat.

15. The diaper defined in claim 1, wherein said flexible sheet is formed as a shower cap.

16. A diaper wrapper especially adapted for enclosing and sealing a diaper when soiled, said diaper wrapper comprising:
(a) a liquid impervious, disc-shaped, flexible sheet with a rounded outer periphery having a first width when laid flat;
(b) an elastic strand secured to said outer periphery of the flexible sheet, said elastic stand forming an endless loop which, in a relaxed state thereof, shapes the flexible sheet into a pouch with an opening inside of said loop having a second width less than or substantially equal to a distance between two side margins of said diaper; and
(c) a pair of flexible strands secured to the flexible sheet on opposite sides of said opening and extending away from each other in opposite directions;
wherein said first width of the flexible sheet is at least twice said second width of said opening such that, when shaped into a pouch, said flexible sheet is thereby caused to assume a round pocket shape having an outer, annular portion folded over with said opening at a center portion thereof;
whereby a diaper, when soiled, may be inserted in said pouch and the opening in said pouch may be closed by tying said flexible strands, thereby wrapping and sealing the soiled diaper.

17. The diaper defined in claim 16, wherein said flexible sheet is substantially circular when laid flat.

18. The diaper defined in claim 16, wherein said flexible sheet is oval-shaped when laid flat.

19. The diaper defined in claim 16, wherein said flexible sheet is formed as a shower cap.

20. A method of producing a disposable absorbent diaper having a wrapper for enclosing and sealing the diaper when soiled, with said wrapper comprising:
(a) liquid impervious, disc-shaped, flexible sheet with a rounded outer periphery, said flexible sheet having a first width when laid flat;
(b) an elastic strand secured to said outer periphery of the flexible sheet, said elastic strand forming an endless loop which, in a relaxed state thereof, shapes the flexible sheet into a pouch with an opening inside of said loop having a second width less than or substantially equal to a distance between two side margins of said diaper; and
(c) a pair of flexible strands secured to the elastic strand on opposite side of said opening and extending away from each other in opposite directions;
wherein said first width of the flexible sheet is at least twice said second width of said opening such that, when shaped into a pouch, said flexible sheet is thereby caused to assume a round pocket shaped having an outer, annular portion folded over with said opening at a center portion thereof;
said method comprising the steps of:
(1) producing a disposable diaper having a front waistband region, a back waistband region, and an intermediate region with two laterally opposed side margins interconnecting the front and back waistband region, the intermediate region of the diaper having a liquid pervious liner, a liquid impervious backsheet and an absorbent core disposed between the liner and the backsheet;
(2) producing said wrapper; and
(3) attaching said annular portion of said flexible sheet of said wrapper to one of said front and back waistband portions of the diaper.

* * * * *